United States Patent
Haake et al.

(10) Patent No.: US 7,041,847 B2
(45) Date of Patent: May 9, 2006

(54) METHOD FOR CLEANING CRUDE TEREPHTHALIC ACID AND CATALYSTS SUITABLE FOR THE SAME AND CONTAINING CARBON FIBERS

(75) Inventors: Mathias Haake, Mannheim (DE);
Ekkehard Schwab, Neustadt (DE);
Michael Koch, Speyer (DE);
Hans-Joachim Müller, Grünstadt (DE);
Manfred Stroezel, Ilvesheim (DE);
Hermann Petersen, Grünstadt (DE);
Peter Schreyer, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 37 days.

(21) Appl. No.: 10/466,478

(22) PCT Filed: Jan. 29, 2002

(86) PCT No.: PCT/EP02/00900

§ 371 (c)(1),
(2), (4) Date: Jul. 16, 2003

(87) PCT Pub. No.: WO02/060851

PCT Pub. Date: Aug. 8, 2002

(65) Prior Publication Data

US 2004/0049073 A1 Mar. 11, 2004

(30) Foreign Application Priority Data

Jan. 31, 2001 (DE) ............................... 101 04 224
Aug. 27, 2001 (DE) ............................... 101 41 848

(51) Int. Cl.
*C07C 51/487* (2006.01)
*B01J 35/06* (2006.01)

(52) U.S. Cl. ...................... 562/487; 502/185; 422/222; 585/250

(58) Field of Classification Search ................ 562/487; 502/185; 422/222
See application file for complete search history.

(56) References Cited

U.S. PATENT DOCUMENTS

| | | | |
|---|---|---|---|
| 3,584,039 A | 6/1971 | Meyer | |
| 5,866,734 A | 2/1999 | Flick et al. | |
| 6,066,589 A | 5/2000 | Malentacchi et al. | |
| 6,383,972 B1 | 5/2002 | Parmentier et al. | |
| 6,436,873 B1 | 8/2002 | Broecker et al. | |

FOREIGN PATENT DOCUMENTS

| | | |
|---|---|---|
| CA | 1173816 | 9/1984 |
| CA | 2090930 | 9/1993 |
| GB | 994769 | 6/1965 |

OTHER PUBLICATIONS

EP 418-682 Abstract.

*Primary Examiner*—Bernard Dentz
(74) *Attorney, Agent, or Firm*—Novak Druce & Quigg, LLP

(57) ABSTRACT

The invention relates to a method for cleaning crude terephthalic acid by means of catalytic, hydrogenating aftertreatment using a catalyst material containing at least one hydrogenation metal applied to a carbon carrier consisting of carbon fibres. The invention also relates to a catalyst consisting of the at least one catalyst material containing the at least one hydrogenation metal applied to the carbon fibres, the BET surface of the carbon carrier being <500 $m^2/g$, and a monolithic catalyst consisting of said at least one catalyst material containing the at least one hydrogenation material applied to the carbon fibres, and at least one support element or skeleton element which differs from the catalyst material and is connected to the same, said element mechanically supporting the catalyst material and maintaining the same in a monolithic form. The invention further relates to a method for producing the monolithic catalyst and the use thereof, a reactor containing a plane catalyst material in the form of woven fabric, knitted fabric and/or felt, the use of the same and a method for the selective hydrogenation of carbon-carbon double or triple bonds and/or hydrogenable functional groups in organic compounds containing the same.

15 Claims, No Drawings

METHOD FOR CLEANING CRUDE TEREPHTHALIC ACID AND CATALYSTS SUITABLE FOR THE SAME AND CONTAINING CARBON FIBERS

This application is a 371 of PCT/EP02/00900 filed Jan. 20, 2002.

The present invention relates to a process for purifying crude terephthalic acid by catalytic hydrogenative after-treatment over a catalyst material comprising at least one hydrogenation metal applied to a carbon support. The invention further relates to a reactor and catalysts comprising carbon fibers, to a process for producing them and to their use as, in particular, a hydrogenation catalyst.

The major part of the terephthalic acid produced industrially is produced by the Amoco liquid-phase oxidation process. In this process, p-xylene is oxidized by atmospheric oxygen under pressure in 95% strength acetic acid with the aid of a catalyst system comprising Co and Mn salts and bromine compounds. In the Amoco process, a purification step is necessary after the oxidation step if the terephthalic acid produced is to be processed further to produce fibers. The task of this purification step is essentially to convert 4-carboxybenzaldehyde formed by only partial oxidation into compounds which do not interfere or are easily separated off. About 5 000 ppm of 4-carboxybenzaldehyde are typically formed. This compound has to be removed because it interferes in the polycondensation reaction in the further processing of the terephthalic acid. In addition, troublesome yellow discoloration of the condensation product also occurs.

The most widespread solution to this problem is a subsequent hydrogenation step in which an aqueous solution of the crude terephthalic acid is treated at about 250° C. under pressure over a noble metal-carbon catalyst. This converts the 4-carboxybenzaldehyde into p-toluic acid which, unlike the aldehyde, can easily be removed from the desired terephthalic acid by crystallization. The basic principle of this process is described in U.S. Pat. No. 3,584,039 (1967). The carbon supports used in the catalyst are pulverulent or granular.

The hydrogenation process is customarily carried out industrially using particulate catalysts which typically comprise from 0.5% by weight of palladium on an industrially available carbon support, cf. EP-A-0 879 641. Although the hydrogenation objective can be achieved satisfactorily in this way, the catalysts used have some disadvantages in practical use. In particular, catalyst beds made up of particulate catalysts based on carbon as support have the disadvantage that, owing to the relatively low mechanical stability of the support material, the unavoidable motion which occurs in the catalyst bed under operating conditions results in abraded material which has to be separated off from the product in a downstream step. In addition, this abraded material is also associated with a loss of the expensive active noble metal component. Furthermore, it is frequently observed that active noble metal component is lost in other ways during the operating time if it has not been fixed chemically to the support material to a sufficient degree.

Fixed-bed catalysts comprising activated carbon fibers on which one or more active catalyst components have been deposited are described in DE-A-32 29 905. The carbon fibers are in the form of a structure in which they are intertwined with one another and form a volume-filling object. Here, the carbon fibers are, for example, in felt-like form.

Monolithic catalysts have been used for hydrogenation for some time. EP-A-0 827 944 describes such a hydrogenation process in which the catalyst is used as catalyst packing, preferably in monolithic form. The catalyst packing is produced by applying at least one substance which is active as catalyst to woven or knitted meshes/fabrics or foils/films as support material.

Coating of the catalyst supports with active compositions can be carried out by various methods. EP-A-0 965 384 describes impregnation processes for applying active composition to structured supports or monoliths. This is carried out using an impregnation medium which has a surface tension of not more than 50 mN/m. Monoliths are produced from the structured supports. The materials used for the support can be metallic or ceramic materials or synthetic polymers, with carbon also being mentioned. As described in EP-A-0 827 944, preference is given to using woven metal mesh strips as catalyst supports or catalysts.

WO 99/26721 describes the production of a catalyst support made of activated carbon fibers. For this purpose, rayon fibers are converted into activated carbon fibers and impregnated with catalytically active metals or treated by cation exchange. Shaping the catalyst support by conversion into woven fabrics and other sheet-like substrates is described. The catalyst is used in this woven form.

An important application of hydrogenation catalysts is the preparation and purification of terephthalic acid.

It is an object of the present invention to provide a process for purifying crude terephthalic acid and to provide hydrogenation catalysts which avoid the disadvantages of the known catalysts. The catalysts should, in particular, have increased mechanical stability and abrasion resistance and should be able to be used advantageously in the hydrogenative after-treatment of crude terephthalic acid.

We have found that this object is achieved by a process for purifying crude terephthalic acid by catalytic hydrogenative after-treatment over a catalyst material comprising at least one hydrogenation metal applied to a carbon support, wherein carbon fibers are used as carbon support.

The catalytic hydrogenative after-treatment can be carried out as described in U.S. Pat. No. 3,584,039. In particular, the catalyst serves to catalyze the hydrogenation of 4-carboxybenzaldehyde to p-toluic acid. The process is particularly preferably carried out at temperatures in the range above 200° C. and under a pressure of preferably from 50 to 100 bar. The hydrogenative after-treatment can be carried out continuously or batchwise.

The carbon fibers can be installed in the reactor in any suitable form. For example, they can be present in the reactor either in ordered or unordered form, for example in unordered form as felt as described in DE-A-32 29 905, or in ordered form as a sheet-like structure as described, for example, in WO 99/26721. Any three-dimensional arrangement of the carbon fibers which allows catalytic hydrogenative after-treatment of crude terephthalic acid can be employed. It therefore has to allow contact of crude terephthalic acid with the carbon fibers and allow mass transfer. For this reason, the carbon fibers are generally installed in such a way that the crude terephthalic acid solution can pass along the carbon fibers during the catalytic hydrogenation.

In a continuous, liquid operation mode, the carbon fibers are therefore preferably installed in the reactor in such a way that the liquid stream runs through the reactor on the carbon fibers. Preferred geometries are described in more detail below.

The catalyst material can, for example, be in sheet-like form as woven or knitted fabrics or meshes and/or felts as parallel fibers or tapes. The parallel fibers or tapes can be aligned along the direction of flow through a reactor.

In one embodiment of the present invention, the sheet-like catalyst material has at least two opposite edges at which the catalyst material is fastened in a reactor so as to retain its shape. A plurality of strips of the sheet-like catalyst material preferably extend parallel to a preferred direction in the reactor and they are arranged relative to one another in space in such a way that abrasion on the strips by contact of the strips with one another or with the reactor walls is largely or preferably completely prevented during operation of the reactor.

The expression "opposite edges" relates to a sheet-like catalyst material which has two edges bounding the sheet on two sides. The edges are essentially parallel to one another. They are preferably straight, but can also have other shapes such as a wave shape or a different type of line. They are preferably parallel to one another, but can also form an angle of, for example, up to 20° with one another. For example, a parallelogram has two pairs of such opposite, parallel edges. A rectangular or square sheet has two pairs of mutually perpendicular, opposite edges which bound the area. The opposite edges are, according to the present invention, configured so that they allow the sheet-like catalyst material to be fastened in a reactor. It is fastened so as to retain its shape. The expression "so as to retain its shape" means that the catalyst material fixed in place in the reactor retains its sheet-like shape before, during and after operation of the reactor and is not pressed together, for instance into a crushed ball or heap. For example, the sheet-like catalyst material can be fixed in place in the reactor in a manner comparable to a square sail of a sailing ship. The sheet-like shape extends through the reactor and is not altered significantly during operation of the reactor.

It is, for example, conceivable for two gratings to be installed in a cylindrical reactor in the upper and lower regions of the reactor perpendicular to the longitudinal axis of the reactor and the sheet-like catalyst material or the fibers or ribbons to be clamped between these. If the mutually parallel gratings have a number of bars, then a plurality of parallel strips of the sheet-like catalyst material can be clamped to these fastening facilities. The expression "strips" refers to essentially rectangular sheets of the sheet-like catalyst material which are fastened, in particular clamped, in this flat, sheet-like form in the reactor so as to retain their shape. A plurality of strips of the sheet-like catalyst material are preferably installed parallel to a preferred direction in the reactor (for instance in a manner comparable to the preferred orientation of liquid crystals in a nematic phase). In the case of a tubular reactor, the preferred direction can, for example, run along the longitudinal direction of the tube. However, the preferred direction can also be at an angle to the longitudinal direction of the reactor. The strips are preferably installed in the reactor so that their preferred direction essentially coincides with the flow direction of a reaction mixture.

The strips are preferably arranged in the reactor and relative to one another so that abrasion on the strips caused by contact of the strips with one another or with the reactor walls during operation of the reactor is largely prevented. This is ensured by sufficient distances between the strips and from the strips to the walls of the reactor. Suitable geometries can be determined quickly by means of simple experiments. Any abrasion can easily be observed visually in the output from the reactor.

Variations of the geometries mentioned above by way of example, for example woven catalyst strips fixed only in the upper region (hanging freely) or (partly) fixed in a frame, are included within the scope of the invention.

Accordingly, the invention also provides a reactor containing a sheet-like catalyst material in the form of woven or knitted fabrics/meshes and/or felts which comprises at least one hydrogenation metal applied to carbon fibers and has at least two opposite edges at which the catalyst material is fastened in the reactor so as to retain its shape or containing the catalyst material in the form of parallel fibers or ribbons. The reactor with the sheet-like catalyst material present therein preferably has one of the above-described geometries.

In a further embodiment of the invention, a monolithic catalyst as described below is used. The description of the carbon fibers and hydrogenation metals and production methods also apply to the embodiment described above.

In a further embodiment of the present invention, the object of the invention is achieved by a catalyst comprising at least one hydrogenating agent applied to a carbon support, wherein carbon fibers are used as carbon support and the carbon support has a BET surface area of <500 $m^2/g$, preferably <300 $m^2/g$, particularly preferably <100 $m^2/g$, very particularly preferably <50 $m^2/g$ and in particular <10 $m^2/g$. The lower limit of the possible BET surface area of the carbon support is generally the BET surface area of the geometric fiber surface, corresponding to a porosity of 0%.

These carbon fibers have a high mechanical stability, e.g. the tensile strength of these carbon fibers is generally up to about 60,000 bar, preferably from about 13,000 bar to 35,000 bar.

Suitable geometries and further properties of the catalysts of the present invention have already been mentioned above. Suitable hydrogenation metals are specified below.

The object of the invention is also achieved by a monolithic catalyst which comprises at least one catalyst material comprising at least one hydrogenation metal applied to carbon fibers and at least one support or skeletal element which is different from and joined to the catalyst material and supports the catalyst material mechanically and holds it in the monolithic form.

Monolithic structures are described, for example, in EP-A-0 564 830. Monolithic structures differ from particulate catalysts or their supports in that they are made up of significantly fewer parts than the particulate (pulverulent or granular) catalysts. For a given reactor, the catalyst can be used in the form of a single monolith or a plurality of monoliths can be stacked to form the fixed-bed catalyst. However, the number of monoliths is small, for example from 1 to 10 monoliths are used for a catalyst packing. The monoliths generally have relatively large three-dimensional structures through which continuous channels pass. The monoliths can have any suitable external shape, for example cubic, cuboidal, cylindrical, etc. The continuous channels can have any geometry, for example they can be in the form of a honeycomb structure as in an exhaust gas catalyst. Catalyst monoliths are frequently produced by shaping sheet-like support structures, for example by rolling up or creasing the sheet-like structures to form three-dimensional monoliths. Starting from sheet-like substrates, the external shape of the monolith can be easily matched to given reactor geometries.

It has been found that the above-described problems can also be solved in a technically simple and economically advantageous manner by using monolithic catalyst packings as catalyst supports in the fixed-bed hydrogenation in place of the particulate catalyst supports customary in the prior art. For the purposes of the present invention, monolithic structures are, in particular, structures obtained by firstly loading a sheet-like carbon support, for example a woven carbon fiber fabric, with an active hydrogenation metal and further processing the resulting activated fabric in a further step to produce the desired monolithic catalyst body.

Like the strips arranged in the reactor as described above, the monolithic structures obtained make controlled flow through the catalyst bed possible. Rubbing of the catalyst particles against one another is avoided in both cases. The ordered structure of the catalyst bed results in improved opportunities for flow-optimized operation of the catalyst bed with improved mass transfer between the phases present in the reactor. A theoretical treatment of this optimization potential may be found, for example, in "Monoliths in Multiphase Catalytic Processes" (CatTech 3(1999), 24 ff). The monolithic catalysts described there are all based on extruded shaped bodies which pose greater practical difficulties in loading with active metals than do the catalysts proposed here, which are preferably obtainable from sheet-like precursors. In the publication cited, there is merely a statement that it is also possible to produce monolithic structures from thin metal sheets. The production of such monolithic catalysts from sheet-like precursors is described, for example, in EP-A-0 564 830, EP-A-0 827 944 and EP-A-0 965 384. With regard to the three-dimensional configuration of the catalysts of the present invention, reference may also be made to these documents.

The novel monolithic catalysts based on carbon fiber materials are suitable not only for replacement of conventional fixed catalyst beds but also, in particular, as substitutes for catalysts which are used in suspended form on carbon supports. Such catalysts are used, in particular, in numerous hydrogenation processes, especially in the field of fine chemicals. In these, usually batchwise processes, the catalyst has to be separated from the reaction mixture after the reaction is complete. This is carried out either by sedimentation or by filtration. The catalysts of the present invention can be easily removed from the reaction mixture without the customary more or less complicated operations and at the same time display the same hydrogenation activity. This shortens the batch times and improves the economics of the process. In many cases, the reactor previously used for suspension hydrogenation can continue to be used for accommodating the monolithic catalyst block if only minor engineering modifications are made.

The monolithic catalyst of the present invention comprises a combination of a catalyst material and a skeletal or support element.

The support or skeletal element or elements allows/allow stable and permanent shaping of the catalyst material based on carbon fibers. In the catalyst material, the carbon fibers are preferably present in sheet-like form as woven or knitted fabrics/meshes and/or felts. They are particularly preferably present in the form of woven or knitted fabrics/meshes, in particular in the form of woven fabrics or meshes. Suitable carbon fibers are described, for example, in DE-A-32 29 905, WO 99/26721 and Ullmann's Encyclopedia of Industrial Chemistry, Section: Fibers, Synthetic Inorganic, Composite Materials Carbon Fibers. It is possible to use all suitable carbon fibers. Such fibers are obtainable by methods of the prior art, for example from polyesters, polyamides, polyolefins and the like. According to the present invention, particular preference is given to fibers, woven fabrics, knitted fabrics or felts having the following properties: specific density of from 80 to 600 g/m$^2$, thread density of from 3 to 15 threads/cm, thread diameter of from 0.1 to 0.9 mm. Particular preference is given to using high tensile strength fiber bundles. The BET surface areas are preferably less than 300 m$^2$/g, particularly preferably less than 100 m$^2$/g, in particular less than 15 m$^2$/g. The porosity is preferably less than 0.5 ml/g. Such fibers are marketed by, for example, Tenax Fibers. Suitable fibers are described on the Internet under textileworld.com.

The catalyst material is joined to the support or skeletal element. The support or skeletal element provides mechanical support for the catalyst material and holds it in the monolithic form. Woven carbon fiber fabrics in particular frequently do not have sufficiently good mechanical properties, e.g. hardness and shape stability, for use in fixed beds. According to the present invention, they are therefore joined to one or more support or skeletal elements by means of which the catalyst material is stabilized mechanically and held in the desired monolithic form. Deformation caused by mechanical shocks and flow of reactants through the monolith are avoided in this way. The support or skeletal element can have any shape suitable for this application. It can likewise be joined to the catalyst material in any appropriate manner, for example by means of hooks, adhesive bonding, etc., or else by knitting or weaving the carbon fibers together with the support or skeletal element.

The support or skeletal element or elements is/are preferably sheet-like in the form of woven or knitted fabrics/meshes, felts and/or perforated sheets. Furthermore, the sheet-like bodies can be corrugated or creased in a concertina fashion. Particular preference is given to the sheet-like support or skeletal elements and the catalyst material forming alternating layers in the monolithic catalyst. The support or skeletal element can be made up of any suitable materials, for example metals and their alloys, plastics or ceramics. For materials which can be used, reference may be made to the description of catalyst supports in EP-A-0 965 384. The support or skeletal element is particularly preferably in the form of individual, chemically resistant metals.

In one embodiment of the invention, both the catalyst material and the support or skeletal element or elements are preferably in woven form as a sheet-like layer which is shaped to form a cylindrical monolith having a plurality of flow channels parallel to the longitudinal axis of the cylinder.

The catalyst material comprises at least one hydrogenation metal applied to the carbon fibers described. As hydrogenation metals, it is possible to use all metals which catalyze the hydrogenation of organic compounds. They are preferably metals of groups VII and IB of the Periodic Table of the Elements. The hydrogenation metals are applied in customary amounts to the carbon fibers by known methods. Suitable impregnation methods for applying the active composition are described in EP-A-0 965 384. Other methods of applying and fixing the catalyst metals to the carbon fibers can also be employed. The carbon fibers can, for example, be obtained by oxidation of polymer fibers, and the active metals can be applied to or incorporated in the polymer fibers before oxidation. However, they can also be applied subsequently. For example, the monolithic catalyst can be produced using polymer fibers in a suitable form, for example as a woven fabric/mesh, and subsequently oxidizing the polymer material to form carbon fibers or a woven carbon fiber fabric or mesh.

The invention also provides a process for producing the monolithic catalyst by separately producing the catalyst material and at least one support or skeletal element, combining these and shaping them to form a monolith.

Both the monolithic catalysts and the above-described reactors can be used quite generally for the hydrogenation of unsaturated organic compounds. They can also be used for the selective hydrogenation of carbon-carbon double or triple bonds and/or hydrogenatable functional groups in organic compounds in which these are present. Processes for selective hydrogenation are described, for example, in EP-A-0 827 944. Examples of hydrogenatable functional groups are nitro groups, carbonyl groups, carboxyl groups, etc. The selective hydrogenation of carbon-carbon double or triple bonds can, for example, be carried out in the presence of aromatic rings without the aromatic rings being hydrogenated.

The monolithic catalyst of the present invention and the reactor are particularly preferably used for purifying crude terephthalic acid by catalytic hydrogenative after-treatment. The present invention also provides a corresponding purification process.

As catalyst for the hydrogenative after-treatment, particular preference is given to using a monolithic catalyst comprising palladium as noble metal on the carbon fibers. In the case of woven carbon fiber fabrics, the proportion of palladium is preferably from 10 to 5,000 mg of Pd/m² of woven carbon fiber fabric.

The invention is illustrated by the examples below.

EXAMPLES

Example 1

A monolithic Pd carbon catalyst was produced using 0.98 m² of a woven carbon fiber fabric from Tenax Fibers which had been coated a number of times with an aqueous Pd solution. A total of 910 mg of Pd/m² of carbon fabric were applied. This was carried out using the procedure described in EP-A-0 695 384. A Pd-carbon fabric having the following properties was obtained:

Specific weight: 92 g/m²
Pd content: 1%
Specific surface area: 4.4 m²/g

Example 2

Activity test, hydrogenation of hydrodehydrolinanol (HDHL) to hydrolinanol (H-Lin)

A 0.2 m wide and 0.6 m long piece of the woven fabric from example 1 was combined in layers with a corrugated woven stainless steel mesh to produce a cylindrical monolith which contains numerous flow channels parallel to the longitudinal axis of the cylinder. The walls of these channels consist of the woven carbon fabric loaded with noble metal and the woven stainless steel mesh has the task of mechanically stabilizing the monolith.

The monolith obtained was installed in a reactor in which 0.5 kg of pure HDHL was in each case hydrogenated without solvent in a circulation reactor operated batchwise with circulating gas and circulating liquid at cross-sectional throughputs of, in each case, 200 m³/m²/h for the gas and liquid phase.

The following hydrogenation activities were determined by means of GC analysis:

The experiment gave a hydrogenation rate of 17% of HDHL/h, corresponding to an STY of 1.12 kg of HDHL/$l_{cat}$/h. The product mixture remained clear and colorless.

| Time | HDHL | H-Lin | THL | Residue | C/h |
|---|---|---|---|---|---|
| 0 | 99.84 | 0.00 | 0.00 | 0.00 | |
| 30 | 93.26 | 5.95 | 0.23 | 0.00 | |
| 60 | 85.06 | 13.37 | 0.50 | 0.18 | 14.80 |
| 90 | 75.70 | 22.78 | 0.78 | 0.23 | |
| 120 | 67.45 | 30.23 | 1.10 | 0.71 | 16.22 |
| 150 | 57.32 | 39.96 | 1.39 | 0.92 | |
| 180 | 49.27 | 47.14 | 1.75 | 1.54 | 16.88 |

After removal of the catalyst from the reactor, the monolith was obtained in mechanically unchanged form.

Example 3

Hydrogenation of 4-carboxybenzaldehyde in terephthalic acid solution; loss of Pd.

A mixture of 54 g of TPA in 146 g of water was treated with hydrogen at 250° C. over a monolithic catalyst produced as described in example 2 for one week. Both the terephthalic acid fraction which had crystallized and the supernatant aqueous liquid were subsequently analyzed for palladium.

After removal from the reactor, the catalyst block was obtained in mechanically unchanged form; no traces of abraded material were detected in the output from the reactor. Likewise, no traces of Pd could be found in either of the fractions.

Example 4

In a pressure autoclave, 146 g of water and 54 g of technical-grade crude terephthalic acid (2 000 ppm of 4-carboxybenzaldehyde, color: light yellow) were combined with 8 g of the Pd/C fabric produced as described in example 1. The mixture was stirred at 270° C. under 50 bar of hydrogen for 60 hours. The product consisted of white terephthalic acid crystals having a 4-carboxybenzaldehyde content determined by polarography of <50 mg/kg.

We claim:

1. A process for purifying crude terephthalic acid by catalytic hydrogenative after-treatment over a catalyst material comprising at least one hydrogenation metal applied to a carbon support, wherein carbon fibers are used as carbon support and wherein the catalyst is a monolithic catalyst which comprises, in addition to the catalyst material, at least one support or skeletal element which is different from and joined to the catalyst material and which supports the catalyst mechanically and holds it in the monolithic form.

2. A process as claimed in claim 1, wherein the carbon fibers in the catalyst material are present in sheet-like form as woven or knitted fabrics or meshes and/or felts or as parallel fibers or tapes.

3. A process as claimed in claim 2, wherein the sheet-like catalyst material has at least two opposite edges at which the catalyst material is fastened in a reactor so as to retain its shape.

4. A process as claimed in claim 3, wherein a plurality of strips of the sheet-like catalyst material extend parallel to a preferred direction in the reactor and they are arranged relative to one another in space in such a way that abrasion on the strips by contact of the strips with one another or with the reactor walls is largely prevented during operation of the reactor.

5. A process as claimed in claim 4, wherein the strips are arranged in the reactor so that their preferred direction essentially coincides with the flow direction of a reaction mixture.

6. A process as claimed in claim 1, wherein the support or skeletal element is a metal, plastic or ceramic element which is is built into the monolithic catalyst.

7. A process as claimed in claim 1, wherein the support or skeletal element or elements is/are present in the monolithic catalyst in sheet-like form as woven or knitted fabric/meshes, felts and/or perforated sheets.

8. A process as claimed in claim 7, wherein the support or skeletal elements and the catalyst material are present as alternating layers in the monolithic catalyst.

9. A process as claimed in claim 8, wherein the catalyst material is present in the monolithic catalyst in woven form and the support element or elements is/are present in the form of a metal weave as sheet-like layer which is shaped to form a cylindrical monolith having a plurality of flow channels parallel to the longitudinal axis of the cylinder.

10. A monolithic catalyst which comprises at least one catalyst material comprising at least one hydrogenation metal applied to carbon fibers and at least one support or skeletal element which is different from and joined to the catalyst material and supports the catalyst material mechanically and holds it in the monolithic form.

11. The monolithic catalyst as claimed in claim 10, wherein at least one support or skeletal element or metal, plastic or ceramic is built into the monolithic catalyst.

12. A process for producing a monolithic catalyst as claimed in claim 10, by separately producing the catalyst material and at least one support or skeletal element, combining the two and shaping them to form a monolith.

13. A reactor for working of a process as claimed in claim 1 containing a sheet-like catalyst material in the form of woven or knitted fabrics/meshes and/or felts which comprises at least one hydrogenation metal applied to carbon fibers and has at least two opposite edges at which the catalyst material is fastened in the reactor so as to retain its shape or containing the catalyst material in the form of parallel fibers or ribbons.

14. A process for the selective hydrogenation of carbon-carbon double or triple bonds and/or hydrogenatable functional groups in organic compounds in which these are present, which comprises carrying out the hydrogenation in a reactor as claimed in claim 13.

15. A process for the selective hydrogenation of carbon-carbon double or triple bonds and/or hydrogenatable functional groups in organic compounds in which these are present, which comprises carrying out the hydrogenation over a catalyst as claimed in claim 10.

* * * * *